(12) United States Patent
Bielefeld

(10) Patent No.: US 9,192,488 B2
(45) Date of Patent: Nov. 24, 2015

(54) LINER FOR VACUUM SOCKETS, AND USE OF THE LINER

(75) Inventor: Thilo-Mathias Bielefeld, Siedenlangenbeck (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days.

(21) Appl. No.: 12/742,109

(22) PCT Filed: Nov. 12, 2008

(86) PCT No.: PCT/DE2008/001874
§ 371 (c)(1),
(2), (4) Date: May 10, 2010

(87) PCT Pub. No.: WO2009/062489
PCT Pub. Date: May 22, 2009

(65) Prior Publication Data
US 2010/0249950 A1 Sep. 30, 2010

(30) Foreign Application Priority Data
Nov. 13, 2007 (DE) .................. 20 2007 015 828 U

(51) Int. Cl.
*A61F 2/78* (2006.01)
*A61F 2/80* (2006.01)

(52) U.S. Cl.
CPC ............ *A61F 2/80* (2013.01); *A61F 2002/7818* (2013.01); *A61F 2002/7837* (2013.01); *A61F 2002/805* (2013.01)

(58) Field of Classification Search
CPC .............. A61F 2/78; A61F 2002/7818; A61F 2002/7806; A61F 2/80
USPC ....................................... 623/27–37
See application file for complete search history.

(56) References Cited

U.S. PATENT DOCUMENTS

| | | | |
|---|---|---|---|
| 4,479,272 A | 10/1984 | Beldzisky | |
| 5,904,722 A * | 5/1999 | Caspers | 623/34 |
| 5,980,577 A | 11/1999 | Radis et al. | |
| 8,080,065 B2 * | 12/2011 | Scussel et al. | 623/33 |
| 2004/0137178 A1 | 7/2004 | Janusson et al. | |
| 2004/0243252 A1 * | 12/2004 | Carstens | 623/34 |
| 2005/0240283 A1 * | 10/2005 | Kania | 623/36 |
| 2007/0213839 A1 * | 9/2007 | Nachbar | 623/26 |

FOREIGN PATENT DOCUMENTS

| | | |
|---|---|---|
| DE | 1733818 | 11/1956 |
| WO | 9621405 A1 | 7/1996 |
| WO | 0121113 A2 | 3/2001 |

OTHER PUBLICATIONS

PCT International Search Report of Mar. 26, 2009 for International Application No. PCT/DE2008/001874.

* cited by examiner

*Primary Examiner* — Bruce E Snow
(74) *Attorney, Agent, or Firm* — Holland & Hart

(57) ABSTRACT

A liner for receiving an amputation stump and for placement within a prosthetic vacuum socket (4). Said liner comprising an inner liner (2) and of an outer liner (3) which are fixedly bonded to each other only in the middle third to a distal third of a length of a liner wall. The outer liner (3) is designed to provide a seal with the prosthetic socket (4).

15 Claims, 2 Drawing Sheets

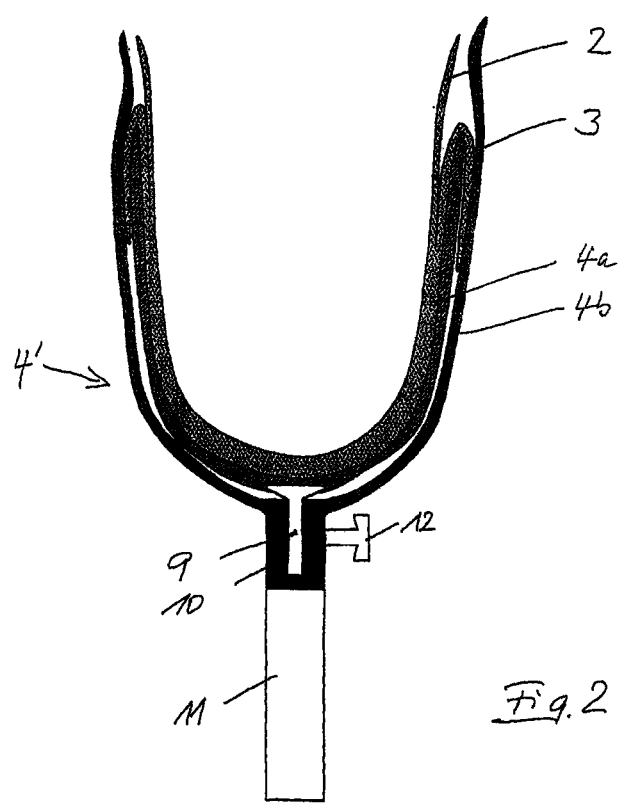

LINER FOR VACUUM SOCKETS, AND USE OF THE LINER

The invention relates to a liner for vacuum sockets for receiving amputation stumps and for use in prosthetic sockets, said liner having a double wall made up of an inner liner and of an outer liner.

The invention further relates to a use of such a liner with a vacuum socket.

In prostheses, and in particular in leg prostheses, it is sought to provide the greatest possible surface area for securing the prosthesis on the amputation stump. That is to say, to ensure that the forces that occur are distributed across the greatest possible surface area, both in the load phase and also in the swing phase. Devices called suction sockets are suitable for achieving the greatest possible surface area for securing the prosthesis. They lie in an airtight manner on the amputation stump. If there is a force that tends to pull the prosthesis from the stump, an underpressure develops which, together with the atmospheric pressure, holds the prosthesis on the amputation stump. In the suction socket, a perfect seal is absolutely essential in order to guarantee the fixing. Otherwise, the underpressure fails and the amputation stump slips out of the prosthesis socket.

It will be clear from this that such an event can cause the prosthesis wearer to fall, because the prosthesis is no longer fixed on the amputation stump.

Since the stump volume can change significantly over the course of a day, as a result of temperature, blood pressure and other medical factors, a one hundred percent seal is not always ensured. It can therefore happen that a prosthesis fits one day and does not fit another day. This variation in volume can even arise within the space of a few hours, and in difficult cases the stump changes on a daily basis. This results in the danger already mentioned.

To avoid this, it is customary to use a liner. These liners are rolled up onto the amputation stump and are provided at their distal end with a fixing pin, which locks the liner into a catch mechanism of the socket. By virtue of the gastight and frictional fit, the liner sits firmly on the amputation stump. This fixing arrangement results in a so-called milking effect if the prosthesis socket is tensioned, since the liner narrows because of its resilience. Standard vacuum liners available on the market do not cover the complete stump surface for a vacuum between liner and socket.

The object of the invention is to improve the build-up of the vacuum between liner and socket wall.

According to the invention, this object is achieved by the liner of the type mentioned at the outset being characterized in that the inner liner and the outer liner are fixedly connected to each other in the middle third and/or distal third, and in that the outer liner is designed to provide a seal with the prosthetic socket.

The liner according to the invention affords the advantage that the entire socket surface can be used for the build-up of the vacuum between liner and socket wall, since the seal is provided by the outer liner, while the inner liner can adapt closely to the amputation stump. By this fixed formation of the vacuum between liner and socket wall, it is possible to do without distal locking using a steel pin and a catch mechanism.

The invention is explained in more detail below on the basis of illustrative embodiments depicted in the drawing, in which:

FIG. 2 shows a second illustrative embodiment of a liner according to the invention.

Figure 1:
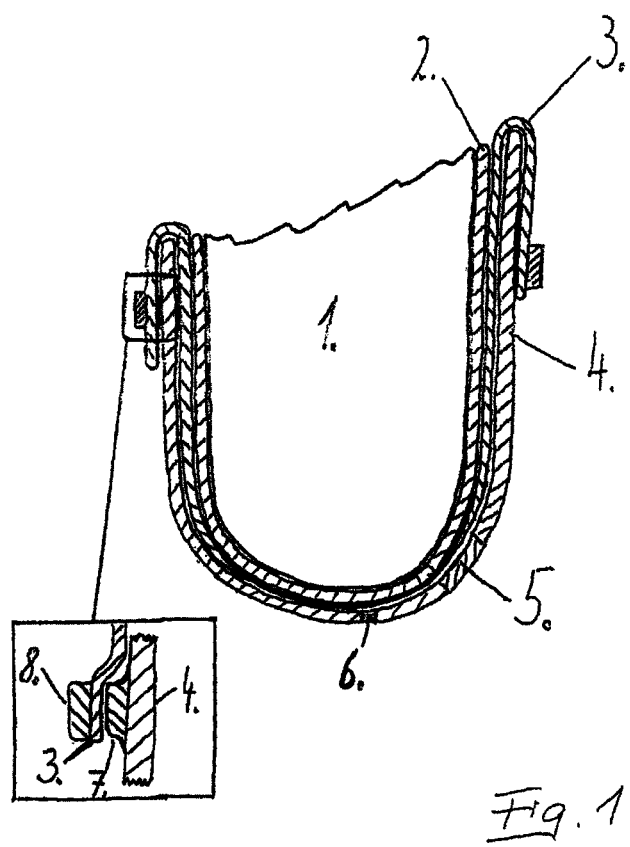
FIG. 1 shows a first illustrative embodiment of a liner according to the invention.

The liner shown in FIG. 1 is composed of an inner liner 2, which is fixedly connected to an outer liner 3 in the middle third to distal third at a closed distal end of the liner and separated from the outer liner 3 at an open proximal end of the liner, the inner liner in this case still having a standard starting length. The liner can have a liner-specific distal configuration with which a longitudinal travel is prevented, an individual distal cup is fitted and a necessary transverse stretch is ensured, etc.

To apply the liner, the complete liner is turned inside out and the inner liner 2 is rolled up onto the stump. Thereafter, the individual, proximal profile of the edge of the inner liner can be fixed and the inner liner correspondingly shortened. The outer liner 3 is now turned back in the proximal direction, and the amputation stump 1 with the rolled-up liner is inserted into the socket 4. The outer liner 3 is now turned back in the distal direction over the socket edge profile 4 and provides a seal on the outside of the socket 4, in order in this way to create the vacuum between socket 4 and liner 2, 3 over the entire inner surface of the socket. The liner is then shortened individually on the outside. To increase the vacuum, a commercially available release valve 5 can be fitted into the socket 4 and/or a commercially available vacuum pump can be used via a connector 6 in the socket 4.

Optionally, an additional circular thickening 7, in the sense of a sealing lip, can be mounted on the outside of the prosthesis socket and promotes the seal of the outer liner with respect to the inside of the socket. In addition, a circular mechanical binding 8 can also be placed from the outside onto the outer liner in the area of the sealing lip in order to increase the leaktightness.

The so-called milking effect is greatly reduced, and the forces that occur are distributed over a greater surface area and are thus greatly reduced per square centimeter. The integral vacuum further ensures that the stump variations are greatly reduced or even avoided. This affords greater comfort when wearing the prosthesis and also permits longer wearing times for prosthesis wearers with variations of the stump volume.

The liner according to the invention is preferably made of silicone elastomers, thermoplastic copolymer gels or polyurethane gels. These materials also permit a subsequent modification of the height to which the inner liner 2 and outer liner 3 are connected to each other, by means of the inner liner and outer liner being subsequently adhesively bonded as far as a desired height. The liner can also be made from suitable combinations of materials.

The liner according to the invention can advantageously be used with a double-walled socket 4', as is shown in FIG. 2. Here, the turned-back edge of the outer liner 3 can protrude into the space between the socket walls 4a, 4b of the double-walled socket 4' and be sealed there. The inside face of the outer liner 3 can in this case be advantageously coated with a textile or with a friction-reducing layer. Particularly in the turned-back area of the outer liner 3, the latter is protected against wear by virtue of the applied textile layer or friction-reducing layer, particularly also in the case of the double-walled prosthesis socket 4'.

Of course, the liner 2, 3 can also be coated on its outside face with a friction-reducing layer or a textile, in order to make the insertion into the prosthesis socket 4 easier. Since the coating may impede the sealing action of the outer liner 3 in the area of the turned-back edge, it is expedient if the coating of the outside face ends well below the height of the prosthesis socket 4, for example at the line up to which the inner liner 2 and outer liner 3 are connected to each other.

As FIG. 2 illustrates, an inside wall 4a of the socket 4' is shorter in the proximal direction than the outside wall 4b. The outside wall 4b is also substantially rigid, whereas the inside wall 4a, although not extensible, can be easily deformed, such that an adaptation to an irregular shape of the amputation stump 1 is possible. The inside wall 4a has, at the distal end, an integrated locking pin 9, which engages with a corresponding lock 10 at the distal end of the outside wall 4b in order to establish a connection. The lock 10 is located on a modular tube 11. The connection between locking pin 9 and lock 10 can be released by an unlocking button 12. In the case of a double-walled socket 4', the outside wall 4b has what is exclusively a supporting function, with the result that the outside wall 4b does not have to be made continuous. It is thus also possible to provide a supporting frame structure as outside wall 4b.

The invention claimed is:

1. A liner comprising;
an inner liner and an outer liner;
a liner wall sitting firmly on the amputation stump when the liner is donned, the liner wall comprising the inner liner and the outer liner each having a closed distal end that extends over and covers a distal end of the amputation stump and an open proximal end to permit insertion of the amputation stump, the inner and outer liners being fixedly bonded directly to each other only in an area within a middle third to a distal third of a length of the liner wall at the closed distal ends so as to be donned together as a single liner over an amputation stump and then inserted into a vacuum socket, and being separated in a proximal third of the liner wall, the outer liner providing a seal with the vacuum socket and the inner liner being closely fitted to the amputation stump.

2. The liner of claim 1, wherein the seal provided by the outer liner is positionable at an edge or on an outside of the vacuum socket.

3. The liner of claim 2, wherein the outer liner is configured to bear on the outside of the vacuum socket via an edge of the outer liner that is turned back in a distal direction.

4. The liner of claim 3, wherein the outer liner is configured to contact a sealing lip that is secured in a gastight manner on the outside of the vacuum socket to provide the seal with the vacuum socket.

5. The liner of claim 4, further comprising a circular binding applied at a height of the sealing lip is configured to increase a contact pressure of the outer liner to the vacuum socket.

6. The liner of claim 5, wherein the vacuum socket includes an inside wall and an outside wall, wherein the outer liner is configured to turn back over an edge of the inside wall and protrude into a space between the inside wall and the outside wall of the vacuum socket.

7. The liner of claim 1, wherein the inner and outer liners are fixedly bonded to each other with an adhesive.

8. The liner of claim 1, wherein the inner and outer liners are fixedly bonded to each other with an adhesive between the area within the middle third to the distal third of the length of the liner wall at the closed distal ends.

9. A liner designed for being donned over an amputation stump and inserted into a vacuum socket, the liner comprising:
an inner liner;
an outer liner;
a liner wall comprising the inner liner and the outer liner;
wherein the inner and outer liners each have a closed distal end that extends over and covers a distal end of the amputation stump and an open proximal end to permit insertion of the amputation stump, the inner and outer liners being fixedly bonded directly to each other only in an area within a middle third to a distal third of a length of the liner and being separated along an open proximal third of the liner;
wherein the liner is configured to be donned over the amputation stump and then inserted into the vacuum socket, the outer liner providing a seal with the vacuum socket and the inner liner being closely fitted to the amputation stump.

10. The liner of claim 9, wherein the seal provided by the outer liner is positionable at an edge or on an outside of the vacuum socket.

11. The liner of claim 10, wherein the outer liner is configured to bear on the outside of the vacuum socket via an edge of the outer liner that is turned back in a distal direction.

12. The liner of claim 11, wherein the outer liner is configured to contact a sealing lip that is secured in a gastight manner on the outside of the vacuum socket to provide the seal with the vacuum socket.

13. The liner of claim 12, further comprising a circular binding applied at a height of the sealing lip is configured to increase a contact pressure of the outer liner to the vacuum socket.

14. The liner of claim 13, wherein the vacuum socket includes an inside wall and an outside wall, wherein the outer liner is configured to turn back over an edge of the inside wall and protrude into a space between the inside wall and the outside wall of the vacuum socket.

15. The liner of claim 9, wherein the inner and outer liners are fixedly bonded to each other with an adhesive.

* * * * *